United States Patent
Robioneck

(10) Patent No.: US 6,579,294 B2
(45) Date of Patent: Jun. 17, 2003

(54) LOCKING NAIL FOR FRACTURE FIXATION

(75) Inventor: Bernd Robioneck, Preetz (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/910,378

(22) Filed: Jul. 20, 2001

(65) Prior Publication Data

US 2002/0072748 A1 Jun. 13, 2002

(30) Foreign Application Priority Data

Jul. 26, 2000 (DE) ..................................... 200 12 877 U

(51) Int. Cl.[7] ............................................... A61B 17/56
(52) U.S. Cl. .......................... 606/64; 606/62; 606/67; 606/65
(58) Field of Search .......................... 606/64, 60, 62, 606/63, 65, 66, 67, 68

(56) References Cited

U.S. PATENT DOCUMENTS

| | | | |
|---|---|---|---|
| 4,281,649 A | * | 8/1981 | Derweduwen ............... 606/64 |
| 4,622,959 A | | 11/1986 | Marcus |
| 5,176,681 A | | 1/1993 | Lawes et al. |
| 5,312,406 A | | 5/1994 | Brumfield |
| 5,454,813 A | * | 10/1995 | Lawes .......................... 606/62 |
| 6,221,074 B1 | * | 4/2001 | Cole et al. ................... 606/60 |

FOREIGN PATENT DOCUMENTS

| | | |
|---|---|---|
| DE | 85 28 770 U1 | 1/1986 |
| DE | 3541597 C2 | 9/1987 |
| DE | 3541597 | * 9/1987 |
| EP | 0 321 170 B1 | 11/1994 |

* cited by examiner

Primary Examiner—Pedro Philogene
(74) Attorney, Agent, or Firm—Lerner, David, Littenberg, Krumholz & Mentlik, LLP

(57) ABSTRACT

A locking nail includes a shank, at least one cross-bore close to one end and at least one cross-bore close to the other end. The cross-bores for receiving a bone screw each. An additional cross-bore located at one end of the nail is of an elongate shape in the longitudinal direction of the nail. A female thread is formed in a hollow-designed shank portion having the elongate cross-bore. A locking member with a male-threaded portion which is adapted to be screwed into the female thread in the hollow portion and interact with the bone screw in the elongate cross-bore in order to displace it transversely to its longitudinal axis in the cross-bore. A second cross-bore is provided for a bone screw between the elongate cross-bore and the adjacent end of the shank. The arrangement of the female thread is such and the length of the locking member and the location of the second cross-bore are sized such that the locking member largely leaves vacant the second bore even if the bone screw which is in the elongate cross-bore bears against the end of the elongate cross-bore facing the shank end. This allows for the insertion of a second bone screw in the second bore.

12 Claims, 2 Drawing Sheets

LOCKING NAIL FOR FRACTURE FIXATION

BACKGROUND OF THE INVENTION

The invention relates to a locking nail for fracture fixation.

Locking nails to care for bone fractures are well known. See, for example, U.S. Pat. No. 5,312,406. These nails are inserted into the medullar space in the bone canal which was prepared or bored open and are inserted from the proximal or distal end of the bone. The nails are locked in the bone, in case of femoral fractures with cross-locking screws. Interlocking is performed by passing bone screws through cross-bores at the ends of the nail shank. This causes the locking nail to axially hold the bone components together and also keeps the bone segments from rotating.

Such locking nails have become known, for example, from U.S. Pat. No. 4,622,959. Further, it is known to employ such locking nails for the guidance and retention of femoral neck screws as has become known, for example, from U.S. Pat. No. 5,176,681 and EP 0 321 170 or German Utility Model G 85 28 770 U1.

Finally, it also has become known to provide such locking nails with a device to allow compression as has become known from German patent DE 35 41 597 or U.S. Pat. No. 4,281,649, the teaching of which is incorporated herein by reference. The proximal end of the locking nail mostly has an elongate cross-bore, and a female thread is provided in the hollow end portion of the nail shank to receive a compression screw with the aid of which the bone screw may be displaced in the elongate cross-bore in parallel with its axis.

SUMMARY OF THE INVENTION

It is the object of the invention to improve a compression type locking nail to the effect that it has an improved locking performance despite its compressive characteristic.

In the locking nail of the present invention a second cross-bore for a bone screw is provided between the elongate cross-bore and the end of the nail shank facing it. In addition, the female thread for the locking member is between the elongate cross-bore and the second cross-bore and the distance between bores and the length of the locking member are chosen to be such that the locking member allows the passage of a bone screw through the second cross-bore even when the bone screw is at the end or close to the end of the elongate cross-bore which faces the near end of the nail shank or the second cross-bore. After the nail is inserted and the cross-bores are found in the bone canal by means of an aiming apparatus, the bone screw for the elongate cross-bore will be inserted as well. Its position expediently is such as to enable the bone screw in the elongate cross-bore to be displaced in parallel with itself or axially with the nail subsequently with the aid of the locking member. This causes compression at the point of fracture. After this operation is completed another bone screw may be passed through the second cross-bore and the nail may be appropriately locked.

The second cross-bore, at the end of the nail shank, leaves sufficient space for another female thread into which the aiming apparatus and/or a drive-in and extraction instrument may be screwed.

From the previously mentioned EP 0 321 170 and U.S. Pat. No. 5,176,681, the teaching of which is incorporated herein by reference, it has already been known to provide two threaded portions on the nail shank of a locking nail to pass through a femoral neck screw. The threaded portion which is placed more inwardly serves for positioning a securing screw by which the femoral neck screw is kept from rotating. The outer threaded portion serves for receiving the aiming apparatus or a drive-in or extraction instrument.

According to an aspect of the invention for a tibia nail, the axis of the second cross-bore is offset from the axis of the elongate cross-bore by an angle which preferably is 90°.

BRIEF DESCRIPTION OF THE DRAWINGS

The invention will now be explained in more detail with reference to an embodiment shown in the drawings.

DETAILED DESCRIPTION OF THE PREFERRED EMBODIMENTS

Figure 1:
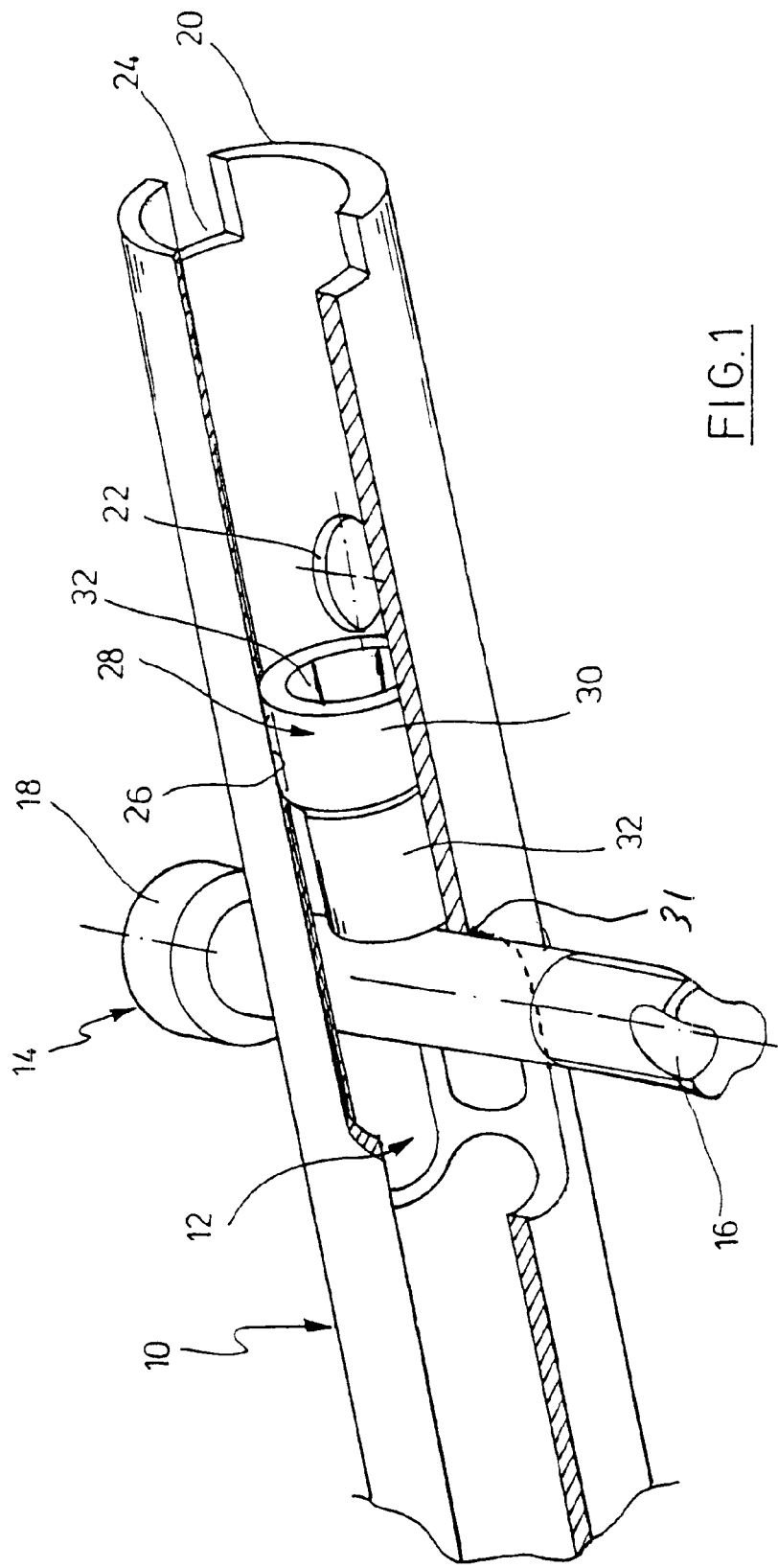
FIG. 1 shows the end of a tibia nail in a perspective view which is partially broken away.
Figure 2:
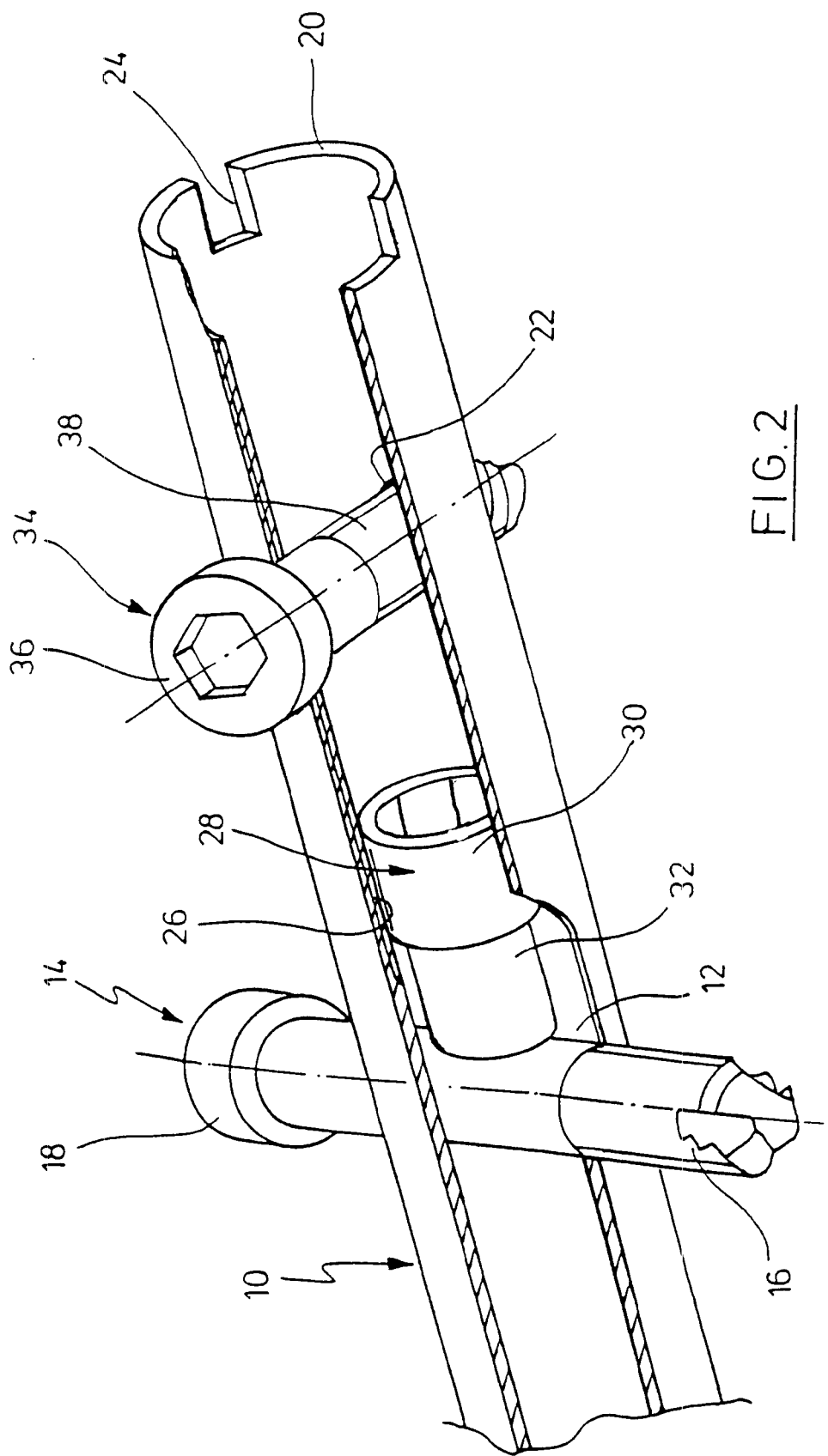
FIG. 2 shows a view similar to FIG. 1, but following compression and the insertion of a second bone screw through the second cross-bore.

Referring to FIGS. 1 and 2, the end portion 10 of a locking nail is shown (which, depending on application, is the proximal or distal end of the nail, it also being the end to which an aiming apparatus and/or a drive-in instrument is connected). As can be seen the nail portion 10 is hollow. The rest of the locking nail, which is not shown, may also be designed to be hollow. In the distal portion which is not shown, the locking nail may have one, two or three cross-bores for cross-locking screws as is well known in the art. In the portion 10, the locking nail has an elongate cross-bore 12 through which a bone screw 14 is passed with a self-cutting threaded portion 16 and a head 18 having countersunk surfaces for a driver (not shown).

In the preferred embodiment, at a distance from the end 20 of the end portion 10, which is proximal as shown and between the end 20 and the elongate bore 12, a second cross-bore 22 is provided the axis of which extends approximately perpendicular to the axis of the elongate cross-bore 12. In the preferred embodiment, second bore 22 is circular and accommodates a bone screw such as bone screw 34. The proximal end is provided with opposed recesses 24 which are engageable with mating projections of an aiming apparatus (not shown) or a drive-in or extraction instrument. The latter are given a predetermined rotational position with respect to the locking nail by the recesses 24.

In the preferred embodiment, a female-threaded portion 26 is formed between the cross-bores 12 and 22 in the canal of the nail portion 10 and a locking member 28 or set screw having a threaded portion 30 and a smaller-diameter non-threaded portion 32 is disposed between the cross-bores 12, 22. In the preferred embodiments, the bores 12, 22 are oriented at about 90°. The length of the locking member 28 is sized such as not to extend into the region of the second cross-bore 22 even if as is shown in FIG. 1, the bone screw 14 is at the proximal end 31 of the elongate cross-bore 12 which faces the second cross-bore 22. The threaded portion is in engagement with the female thread 26. At the right-hand end, the locking member 28 has countersunk engagement surfaces 32 (an inner hexagon) for a tool to enable it to be displaced in the nail canal as can be seen from FIG. 2. FIG. 2 shows is how the locking member 28 has helped in displacing the bone screw 14 in parallel with itself (i.e. along the longitudinal axis of the nail) up to the other end of the elongate cross-bore 12. This will rarely happen in a conventional application. Rather, the bone screw 14 will merely be displaced over a fraction of the length of the elongate cross-bore 12 along the nail longitudinal axis.

Once compression is completed a second bone screw 34 having a head 36 and a threaded shank 38 may be passed through the second cross-bore 22 in order to lock the end of the nail.

As was previously mentioned it is common to place a insertion instrument or even the aiming apparatus for the locking nail onto the associated end of the nail and to bolt it there. Now, it is an advantage for the aiming apparatus to be allowed to remain on the nail end during the compressing operation. The compressing operation is performed by rotating locking member 28 in associated thread 26 by means of a screw-driver or the like.

To this end, the shank of the screw-driver is introduced into the hollow end of the nail. Prior to this, the screw by which the aiming apparatus was located at the proximal nail end has been removed. As was mentioned, however, the aiming apparatus will remain at the nail end during compression. At this point, the shank of the screw-driver is passed through that portion in which otherwise the aiming apparatus screw is seated when the aiming apparatus is mounted at the nail end.

In the preferred embodiment, once the compressing operation is completed the handle is removed from the screw-driver. Now, the design of the shank of the screw-driver is such and the size of the hollow bolt or nut for mounting the aiming apparatus is such that it may be pushed over the screw-driver shank. This allows the surgeon to re-bolt the aiming apparatus to the nail with the screw-driver shank being left where it was. Thus, the shank has a guide function in re-bolting the aiming apparatus. Subsequently, the shank may be removed by simply stripping or pulling it off. Now, the aiming apparatus is fixedly connected to the nail again and the location of the second cross-bore 22 may be determined in a known manner. When this is done bone screw 34 is mounted in the second cross-bore 22 in a standard manner.

The detailed construction of the aiming apparatus, itself, is not relevant. The only essential thing is that the mounting of the aiming apparatus which may be similar to that of U.S. Pat. No. 5,176,681 guarantees for the function described.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A locking nail comprising a longitudinally extending shank with first and second ends, at least one cross-bore close to one end and at least one cross-bore close to the other end each for receiving a bone screw, wherein one cross-bore at one end is of an elongate shape in the longitudinal direction of the nail, a first female thread formed inside a hollow shank portion having the elongate cross-bore, and a locking member with a male-threaded portion which is adapted to be screwed into the first female thread and interacts with a first bone screw associated with said elongate cross-bore in order to displace it transversely to a longitudinal axis of said bone screw in the cross-bore, a second cross-bore for receiving a second bone screw is provided between the elongate cross-bore and the adjacent end of the shank, and that the arrangement of the first female thread, a length of the locking member and the location of the second cross-bore are sized such that the locking member does not block the second bore even if the first bone screw which is in the elongate cross-bore bears against an end of the elongate cross-bore nearest the shank end.

2. The locking nail according to claim 1, wherein the axis of the second cross-bore is offset from the axis of the elongate cross-bore by an angle of 90°.

3. The locking nail according to claim 1, wherein the locking member consists of a threaded portion and a non-threaded portion which interacts with the bone screw in the elongate cross-bore.

4. The locking nail according to claim 1, wherein a second female-threaded portion is provided in the hollow shank portion between the second cross-bore and the adjacent end of the nail shank.

5. The locking nail according to claim 4, wherein the second female threaded portion received a member selected from the group of a driving tool and an extraction tool which tools may be inserted into the hollow shank portion between the second cross-bore and the adjacent end of the nail shank.

6. An instrument for a locking nail according to claim 1, comprising a handle and an elongate shank, which shank can be engaged with the end of the locking member facing it, that the handle can be released from the shank, and that a bolt to mount the aiming apparatus on the nail is shaped such and the diameter of the shank is sized such as to allow the bolt to be pushed over the vacant shank in order to mount the aiming apparatus on the nail with the shank being introduced into or seated within the nail.

7. A method for compressing a fracture in a long bone having a medullary canal comprising:
inserting into the bone canal a longitudinally extending locking nail having first and second ends, with the fracture located therebetween, with at least one cross-bore at the first end and an elongated first bore at the second end, the second end having a hollow internal longitudinal bore intersecting said first elongated cross-bore, said hollow bore having an inner threaded portion for engaging a locking screw, said second end having a second cross-bore located in the longitudinal direction, between said first elongated bore and said second end with said threaded inner portion located between said first elongated bore and said second cross-bore;
inserting a first screw into said elongated bore in a direction generally perpendicular to said longitudinal axis;
inserting a second screw into said cross-bore at said first end of said bone;
inserting a locking screw into said hollow portion of said second end and into engagement with said screw in said elongate bore;
compressing the fracture by moving the screw in the elongated bore towards said first end with said locking screw; and
inserting a third screw into said second cross-bore in said second end with said locking screw located between said third and said first screws.

8. The method as set forth in claim 7 further including attaching an aiming device to said second end of said nail prior to compressing said fracture.

9. The method as set forth in claim 8 further including using said aiming device to insert said first and second screws.

10. The method as set forth in claim 8 further including compressing the fracture with said locking screw with said aiming device attached to said second end.

11. A locking nail comprising a longitudinally extending shank having a hollow first end formed by an internal bore having an open end, an elongated cross-bore extending through said hollow portion, a threaded locking screw having male threads for engaging a female threaded portion of said bore, a generally circular cross-bore extending through said hollow portion, wherein said locking member has a length less than or equal to the distance between the surface of the elongated bore adjacent the open end and the surface of the generally circular bore between said open end and said elongated cross-bore said female threaded portion located between said elongated bore and said generally circular bore.

12. The locking nail as set forth in claim 11 further including a threaded portion located between the open end of said hollow portion and said generally circular bore.

* * * * *